United States Patent
Taepke, II et al.

(10) Patent No.: US 7,963,922 B2
(45) Date of Patent: Jun. 21, 2011

(54) VOLUME DEPLETION DETECTION

(75) Inventors: Robert T. Taepke, II, Coon Rapids, MN (US); Yong K. Cho, Maple Grove, MN (US); Joel R. Lauer, Rogers, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1454 days.

(21) Appl. No.: 11/380,710

(22) Filed: Apr. 28, 2006

(65) Prior Publication Data

US 2007/0255112 A1 Nov. 1, 2007

(51) Int. Cl.
*A61B 5/02* (2006.01)
(52) U.S. Cl. .................... 600/485; 600/483; 600/504
(58) Field of Classification Search .............. 600/481, 600/483–486, 488, 504–507
See application file for complete search history.

(56) References Cited

U.S. PATENT DOCUMENTS

| 5,957,861 | A  * | 9/1999 | Combs et al. ............. 600/547 |
| 2004/0172080 | A1 * | 9/2004 | Stadler et al. ............. 607/17 |
| 2006/0058691 | A1 | 3/2006 | Kiani | |
| 2007/0088220 | A1 * | 4/2007 | Stahmann ................. 600/485 |

FOREIGN PATENT DOCUMENTS

WO WO20070047288 A 4/2007

OTHER PUBLICATIONS

Adamson et al., Ongoing Right Ventricular Hemodynamics in Heart Failure, 2003, Journal of the American College of Cardiology, vol. 41 No. 4, p. 565-571.*
Adamson et al, Ongoing Right Ventricular Hemodynamics in Heart Failure Clinical Value of Measurements Derived from an Implantable Monitoring System, Journal of American College of Cardiology, Elsevier, New York, NY, US, vol. 41 No. 4 (Feb. 19, 2003), pp. 565-571.
Bennett et al, Development of Implantable Devices for Continous Ambulatory Monitoring of Central Hemodynamic Values in Heart Failure Patients, Pace, vol. 28, (Jun. 2005), pp. 573-584.
International Search Report, PCT/US2007/067193, Jun. 2, 2008, 8 Pages.

* cited by examiner

*Primary Examiner* — Charles A Marmor, II
*Assistant Examiner* — Navin Natnithithadha
(74) *Attorney, Agent, or Firm* — Stephen W. Bauer; Reed A. Duthler

(57) ABSTRACT

Detection of volume depletion, particularly after an incidence of volume overload is disclosed. Various methods, systems, and devices are disclosed that sense and analyze a physiological parameter related to a patient's fluid level in order to warn patients of potentially dangerous volume depletion conditions while minimizing false notifications.

10 Claims, 5 Drawing Sheets

VOLUME DEPLETION DETECTION

BACKGROUND

Patients having such conditions as heart failure or decreased kidney function requiring dialysis often have undesirable fluid accumulation in the body. In general, fluid accumulation is a failure or over-response of the homeostatic process within the body. The body normally prevents the build up of fluids by maintaining adequate pressures and concentrations of salt and proteins and by actively removing excess fluid. Fluid accumulation can occur, for example, when the body's mechanisms for preventing fluid accumulation are affected by disease, such as heart failure, left sided myocardial infarction, high blood pressure, altitude sickness, emphysema (all which affect pressures), cancers that affect the lymphatic system, kidney failure, and diseases that disrupt the protein concentrations. As a result, providing an adequate monitor of the patient's fluid status can provide physicians and patients with a better tool to manage disease.

Patients with conditions that contribute to fluid accumulation in the body often uses diuretics to control the fluid level in the body. This can be a delicate balancing act, since fluid accumulation can result in frequent and lengthy hospitalization and overuse of diuretics or other fluid reduction tools can result in dehydration. In some cases, dehydration may become so severe as to result in hypovolemic shock, with symptoms including diminished consciousness, lack of urine output, cool moist extremities, a rapid and feeble pulse (the radial pulse may be undetectable), low or undetectable blood pressure, and peripheral cyanosis.

DETAILED DESCRIPTION

Figure 1:
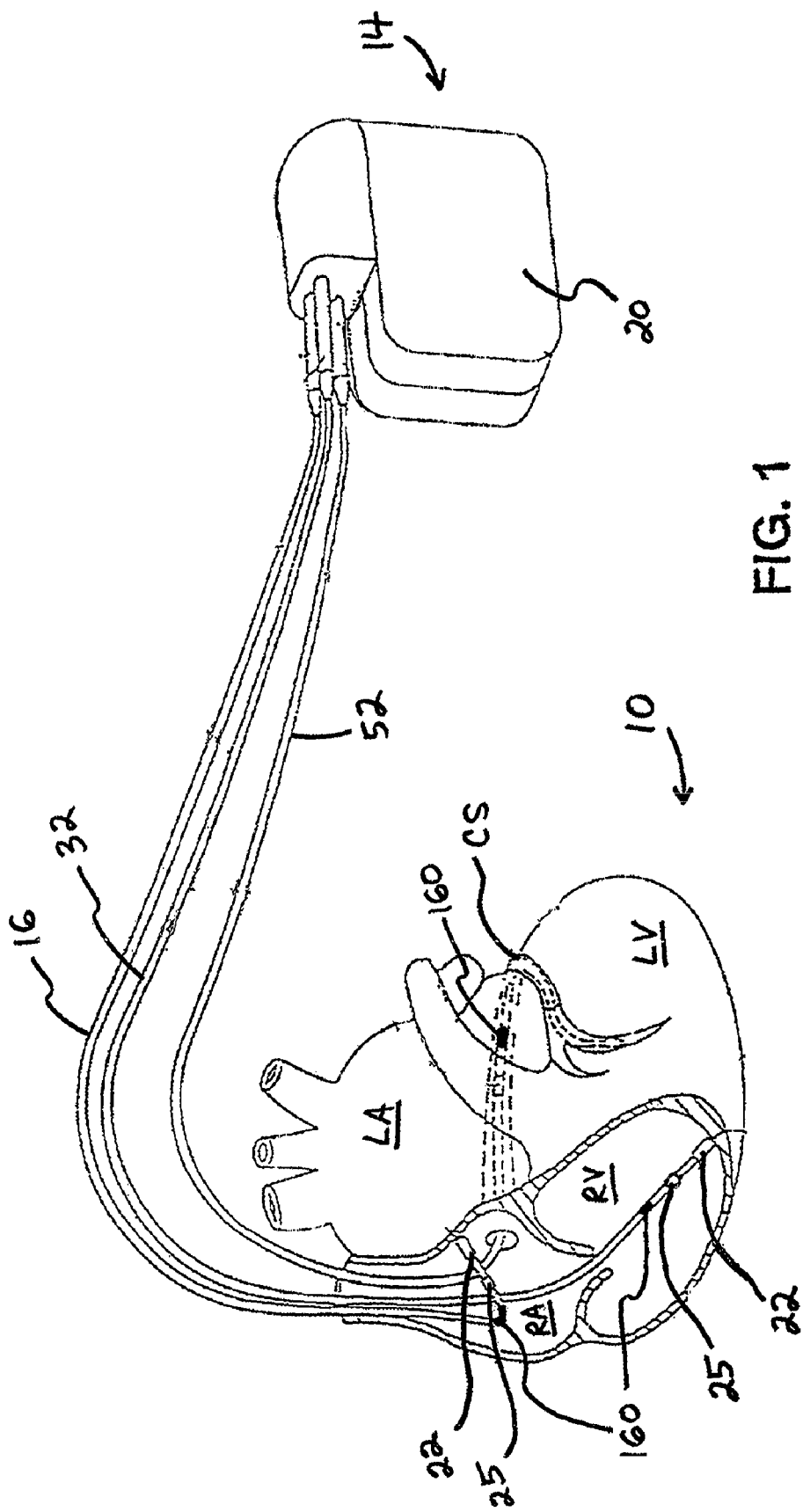
FIG. 1 is a schematic diagram depicting a multi-channel, atrial and bi-ventricular, monitoring/pacing implantable medical device (IMD) in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Fluid Accumulation ("volume overload" or "VO") and dehydration ("volume depletion" or "VD") has been typically assessed by monitoring weight gain. In addition, a thoracic fluid accumulation monitor using either an external or internal thoracic impedance measurements has also been proposed. These measurements have been used to simply monitor the condition or to indicate the need for intervention such as the use of diuretics or dialysis. Because thoracic fluid levels change based on body position and other external influences, measurements often had to be taken at various times of the day (i.e., at night and day times or rest and active times) and averaged or otherwise calculated to evaluate the true fluid level in the patient.

It is believed that volume overload typically develops over a longer period of time than volume depletion. Abrupt onset edema or volume overload is possible, but it is an exception to the general rule. It is also believed that most common instances of volume depletion occur as a result of an excessive response to an incident of volume overload. The treatment of a volume overload condition can require a precise dosage of diuretic, and the consequence of an excessive dose can often be the development of a severe or even dangerous volume depletion condition.

Certain embodiments of the invention include an implantable medical device capable of monitoring blood pressure or intracardiac pressure. It is believed that intracardiac pressure correlates well to volume overload and volume depletion and in fact may be a better indicator than impedance in some applications. For instance, after treatment of a volume overload condition with a diuretic it may take time for the body to reabsorb fluid from the surrounding tissue. This may result in an impedance measurement acting as a lagging indicator of the efficacy of the diuretic when compared to a intracardiac pressure measurement that more quickly recognizes the reduction in blood volume.

Turning now to the Figures, FIG. 1 is a schematic representation of an implantable medical device (IMD) 14 that may be used in accordance with certain embodiments of the invention. The IMD 14 may be any device that is capable of measuring hemodynamic parameters (e.g., intracardiac pressure signals) from within a ventricle of a patient's heart, and which may further be capable of measuring other signals, such as the patient's cardiac electrogram (EGM).

In FIG. 1, heart 10 includes the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an implantable cardioverter defibrillator (ICD), a cardiac resynchronization therapy (CRT) device, an implantable hemodynamic monitor (IHM), or any other such device or combination of devices, according to various embodiments of the invention.

Some or all of the leads shown in FIG. 1 could carry one or more pressure sensors for measuring systolic and diastolic pressures, and a series of spaced apart impedance sensing leads for deriving volumetric measurements of the expansion and contraction of the RA, LA, RV and LV.

The leads and circuitry described above can be employed to record EGM signals, intracardiac pressure signals, and impedance values over certain time intervals. The recorded data may be periodically telemetered out to a programmer operated by a physician or other healthcare worker in an uplink telemetry transmission during a telemetry session, for example.

Figure 2:
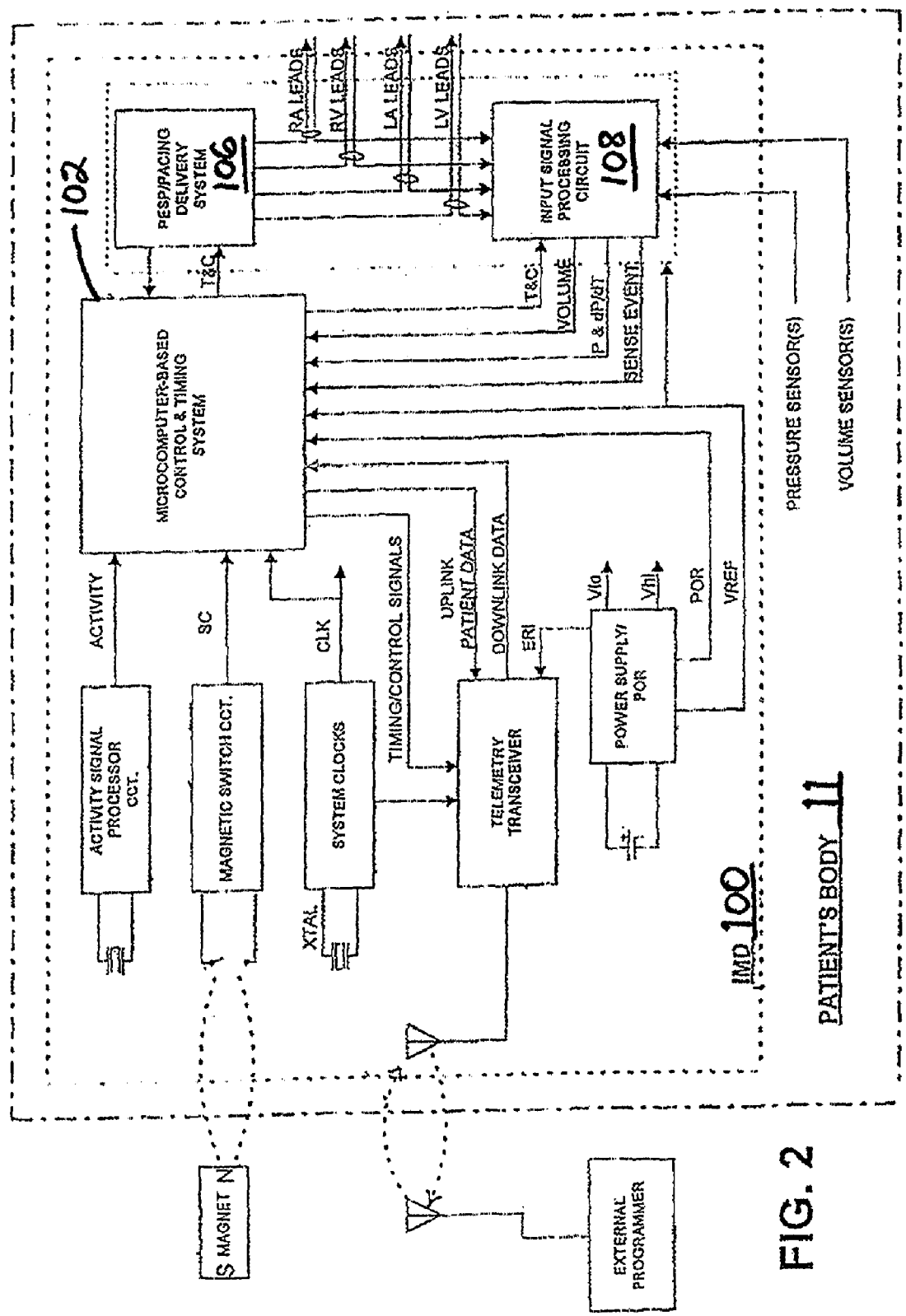
FIG. 2 is a simplified block diagram of an embodiment of IMD circuitry and associated leads that may be employed in the system of FIG. 1 to enable selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 includes a system architecture constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors.

Figure 3:
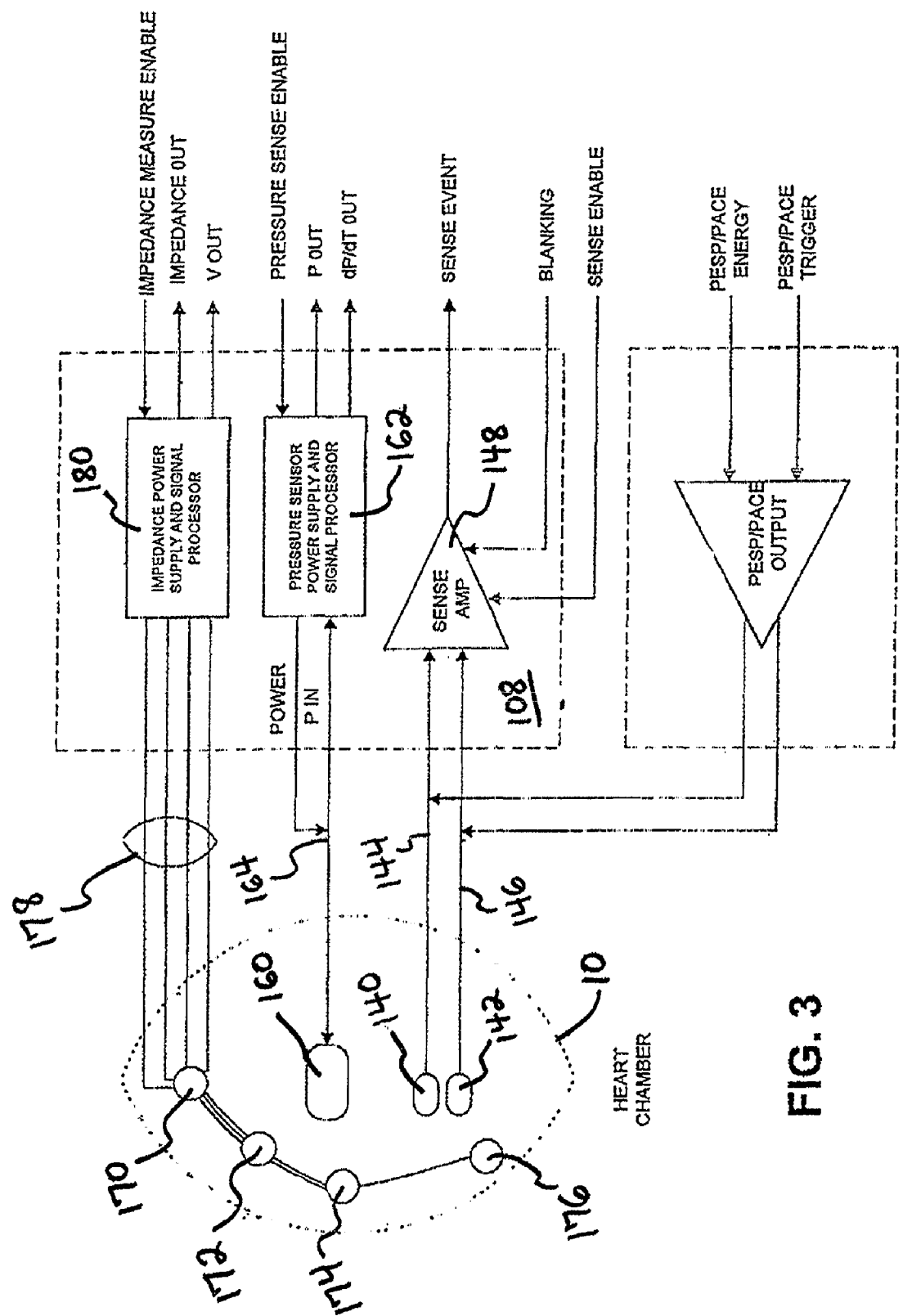
FIG. 3 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored.

The IHM may also store pressure data and calculate a long term and a short term average for the pressure data. An exemplary short term average may be on the order of hours while the long term average may be on the order of 30 days.

The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

Figure 4:
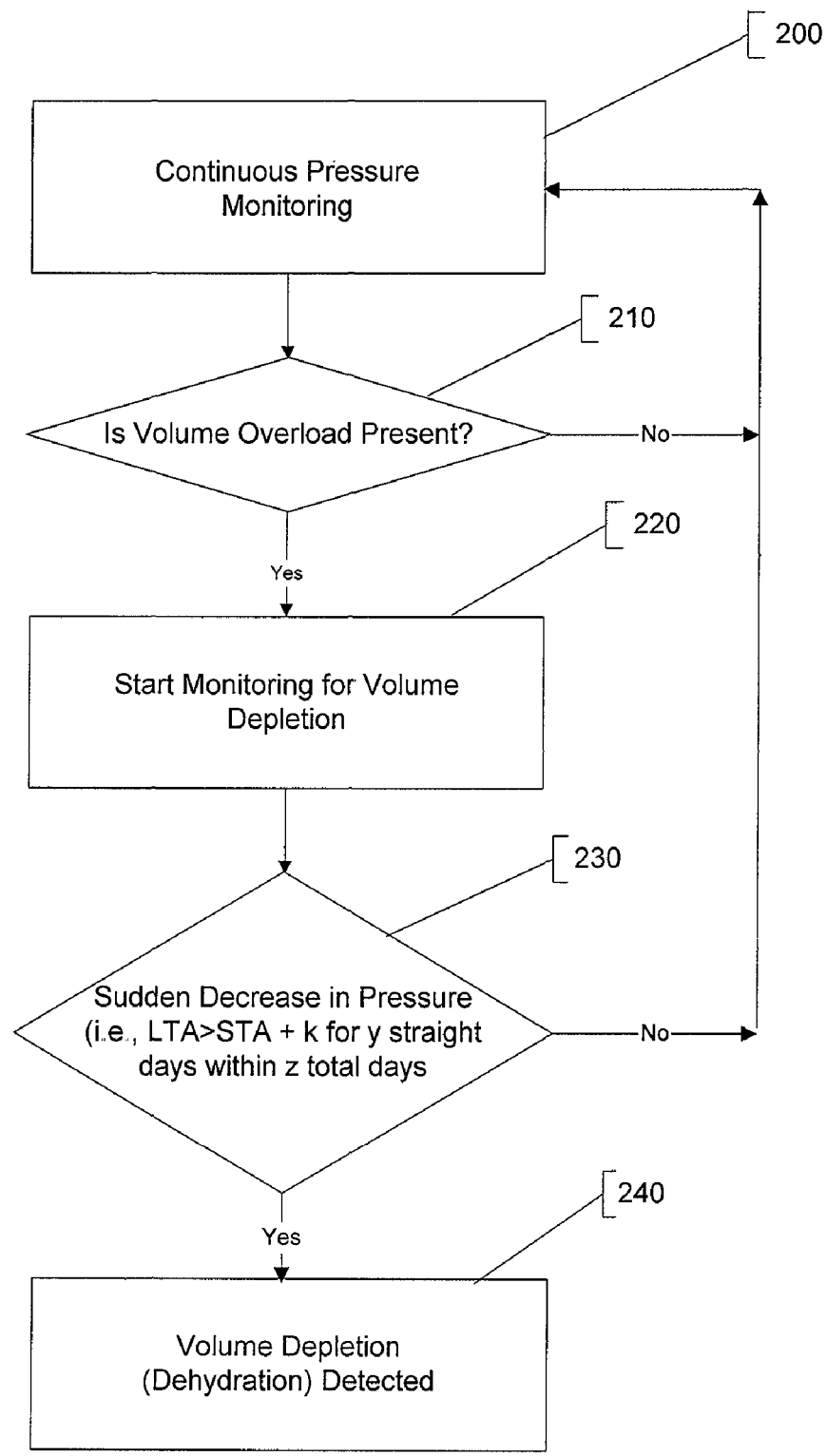
FIG. 4 is a flow diagram of a routine in accordance with embodiments of the invention.

FIG. 4 is a flow diagram of a routine in accordance with embodiments of the invention. The routine begins with continuous pressure monitoring 200. This pressure monitoring could be done by an IHM as described above and could include measurements of right ventricular (RV) systolic and diastolic pressures (RVSP and RVDP), estimated pulmonary artery diastolic pressure (ePAD), pressure changes with respect to time (dP/dt), and others. The routine then determines if volume overload is present 210. This could be determined by any method known in the art. In one embodiment in accordance with the current invention, a short term average and a long term average of a blood pressure measurement are calculated. The routine then determines if the short term average has been greater than the long term average for a certain number of periods. If a short term average, for example a four-hour running average, exceeded a long term average, for example a twenty-day average, for five consecutive days the routine would determine that a volume overload condition is present. This example is illustrative only, and the terms of the averages as well as the duration over which the differential is measured may be modified to any effective values without departing from the claimed invention.

If a volume overload condition is not sensed 210, the routine continues to monitor the pressure 200 and watch for volume overload 210. Only if volume overload is sensed does the routine begin to monitor for volume depletion 220. In one embodiment in accordance with FIG. 4, the routine looks for a sudden decrease in pressure by comparing a short term average pressure to a long term average pressure. In this embodiment, if the short term average pressure is below the long term average pressure by at least a threshold value for a number of days within a predetermined timeframe 230, volume depletion or dehydration, possibly due to over diuresis, has occurred 240. In one exemplary embodiment, a 3-day running average must be below a twenty-day average by a threshold amount for two consecutive days within the seven days following the detection of volume overload 210. If volume depletion is not detected within the predetermined timeframe, the routine stops detecting for volume depletion and returns to continuous pressure monitoring 200. The number of days that are monitored for volume depletion after a volume overload event usually, but not necessarily, fewer than 14 days. By limiting the routine to monitoring for volume depletion only within a predetermined timeframe after volume overload, the routine is less likely to detect false instances of volume depletion because most occurrences of volume depletion are a result of over-treatment of volume overload.

If volume depletion is detected 240, a notification may be given to the patient through an audible alarm, to the patient's caregiver through a radio frequency uplink from a telemetry unit, or by other means. In addition recorded data may be periodically telemetered out to a programmer operated by a physician or other healthcare worker in an uplink telemetry transmission during a telemetry session, for example. This historical data may allow the physician or healthcare worker to modify the parameters of the routine to provide more accurate detection algorithms for a given patient and condition.

Figure 5:
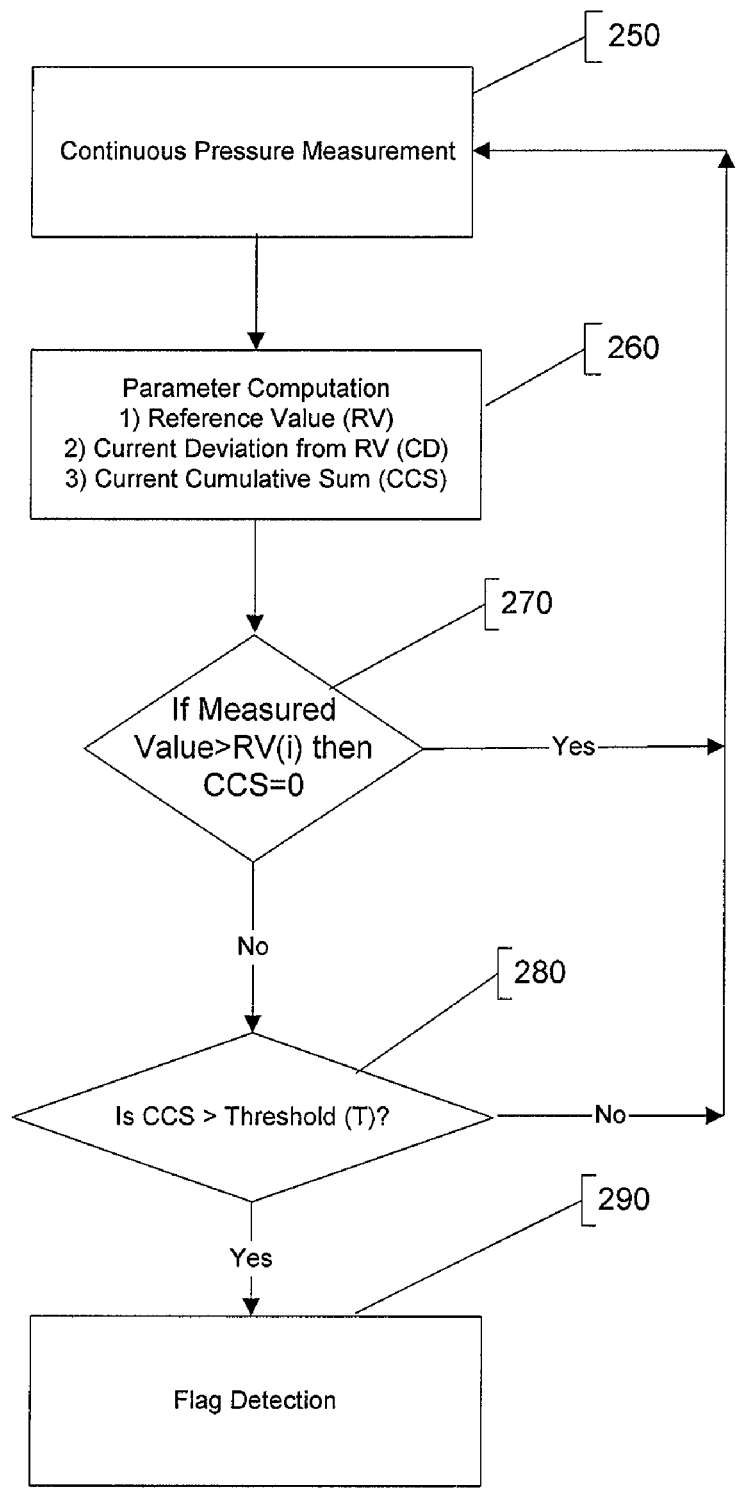
FIG. 5 is a flow diagram of a routine in accordance with embodiments of the invention.

FIG. 5 is a flow diagram of a routine in accordance with embodiments of the invention. The routine of FIG. 5 detects volume depletion and begins with continuous blood pressure measurement 250. This routine may be used to calculate volume depletion after volume overload is detected, either as in the routine in FIG. 4 or by any means known in the art. The routine calculates a reference value (RV), a current deviation from the reference value (CD), and a current cumulative sum of the deviation from the reference value (CCS) over a timeframe 260. Current deviation is in this case is an absolute value of the difference between the measured value and the reference value (no sign). The reference value may be a long term average or adaptive baseline of the pressure measurement or a fixed value determined by a physician. The deviation from the reference may be calculated as an unmodified difference or may involve additional calculation such as scaling using a multiplier and/or an offset.

The routine then compares the measured pressure to the reference value 270. If the measured value is greater than the reference value, the routine resets the cumulative sum to zero and starts over 250. In an optional embodiment, this step 270 may require the measured value to exceed the reference value for multiple readings. If the routine is being used as part of a larger routine that detects volume depletion only after the onset of volume overload, the routine may return to detecting for volume overload if the measured value exceeds the reference value 270.

As long as the measured value remains below the reference value 270, the routine compares the current cumulative sum to a predetermined threshold 280. If the current cumulative sum is less than the threshold, the routine returns to continuous pressure monitoring 250. Once the current cumulative sum exceeds the threshold value 280, the routine flags the detection of volume depletion in a manner known in the art 290.

In another embodiment, one can combine the two examples we provide here by using the cumulative sum algorithm to compute thresholds for the previous embodiment. For example, one can determine volume overload status from the cumulative sum (the same concept in reverse) and activate the depletion detector when volume overload is detected. The depletion detector may use STA and LTA criteria as described previously. In some embodiments, the threshold K used as a threshold or offset as in the formula STA+K<LTA, could be calculated by comparing the normal deviation of the STA about the LTA during periods when the patient is fluid balanced. This K could be actively calculated up to the point where the cumulative sum was last zero—just before raw pressure value was started to deviate (upward) from reference value.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

The invention claimed is:

1. A computer-readable medium programmed with instructions for performing a method in an implantable medical device, the medium comprising instructions for causing a programmable processor to:
   intermittently measure a physiological parameter related to a patient's fluid level to determine measured values;
   calculate long term averages and short term averages of the measured values; and
   compare the short term averages to the long term averages to detect the presence of a volume depletion condition, the detection including calculating a cumulative sum of the difference between the short term averages and the long term averages.

2. A computer-readable medium according to claim 1, further comprising instructions to compare the short term averages and the long term averages to detect the presence of a volume overload condition, the detection of the volume depletion occurring after detecting the presence of the volume overload.

3. A computer-readable medium according to claim 1, wherein the detecting of the volume depletion condition includes comparing the cumulative sum to a predetermined threshold value.

4. A computer-readable medium according to claim 3, further including instructions to reset the cumulative sum to zero when the values of a predetermined number of the short term averages exceed the values of associated long term averages.

5. A computer-readable medium according to claim 1, further including instructions to stop the detection of the volume depletion condition when the values of a predetermined number of the short term averages exceed the values of associated long term averages.

6. A computer-readable medium according to claim 5, wherein the predetermined number of the short term averages are consecutive.

7. A computer-readable medium according to 1, wherein the intermittent measurements include periodic measurements.

8. A system for detecting volume depletion in a patient comprising:
   an implantable sensor for measuring a physiological parameter related to a patient's fluid level and producing a representative signal thereof;
   a processor within an implantable medical device operatively connected to the sensor and receiving the sensor signal, the processor calculating long and short term averages of the sensor signal and comparing the long and short term averages to detect the presence of a volume overload condition, the processor comparing the long and short term averages to detect the presence of a volume depletion condition after detection of the presence of the volume overload condition; and
   an indicator operatively connected to the processor that indicates the detection of the volume depletion condition.

9. A system according to claim 8, wherein the implantable sensor includes a blood pressure sensor that measures intracardiac blood pressure.

10. A system according to claim 9, wherein the blood pressure sensor measures one of at least right ventricular systolic pressure (RVSP) and right ventricular diastolic pressures (RVDP).

* * * * *